United States Patent [19]

Snell

[11] 4,102,179

[45] Jul. 25, 1978

[54] LIQUID COLUMN CHROMATOGRAPHIC SEPARATION

[75] Inventor: James B. Snell, Bartlesville, Okla.

[73] Assignee: Phillips Petroleum Company, Bartlesville, Okla.

[21] Appl. No.: 783,514

[22] Filed: Apr. 1, 1977

[51] Int. Cl.² ............................................ G01N 31/08
[52] U.S. Cl. ................................. 73/61.1 C; 210/31 C
[58] Field of Search ............ 73/61.1 C, 23.1, 422 GC; 210/31 C, 198 C; 55/197, 386

[56] References Cited

U.S. PATENT DOCUMENTS

| | | | |
|---|---|---|---|
| 3,140,615 | 7/1964 | Broerman | 73/422 GC |
| 3,385,101 | 5/1968 | Roof | 73/23.1 |
| 3,394,582 | 7/1968 | Munro et al. | 73/23.1 |
| 3,492,873 | 2/1970 | Broerman | 73/422 GC |

*Primary Examiner*—Richard C. Queisser
*Assistant Examiner*—Joseph W. Roskos

[57] ABSTRACT

A process and apparatus for sequentially subjecting a plurality of liquid samples to column chromatographic separation and analysis wherein the direction of flow of liquid samples in the column is periodically reversed in such a fashion that the characteristics of the sorbent bed are not significantly affected by compacting of the solid sorbent.

17 Claims, 1 Drawing Figure

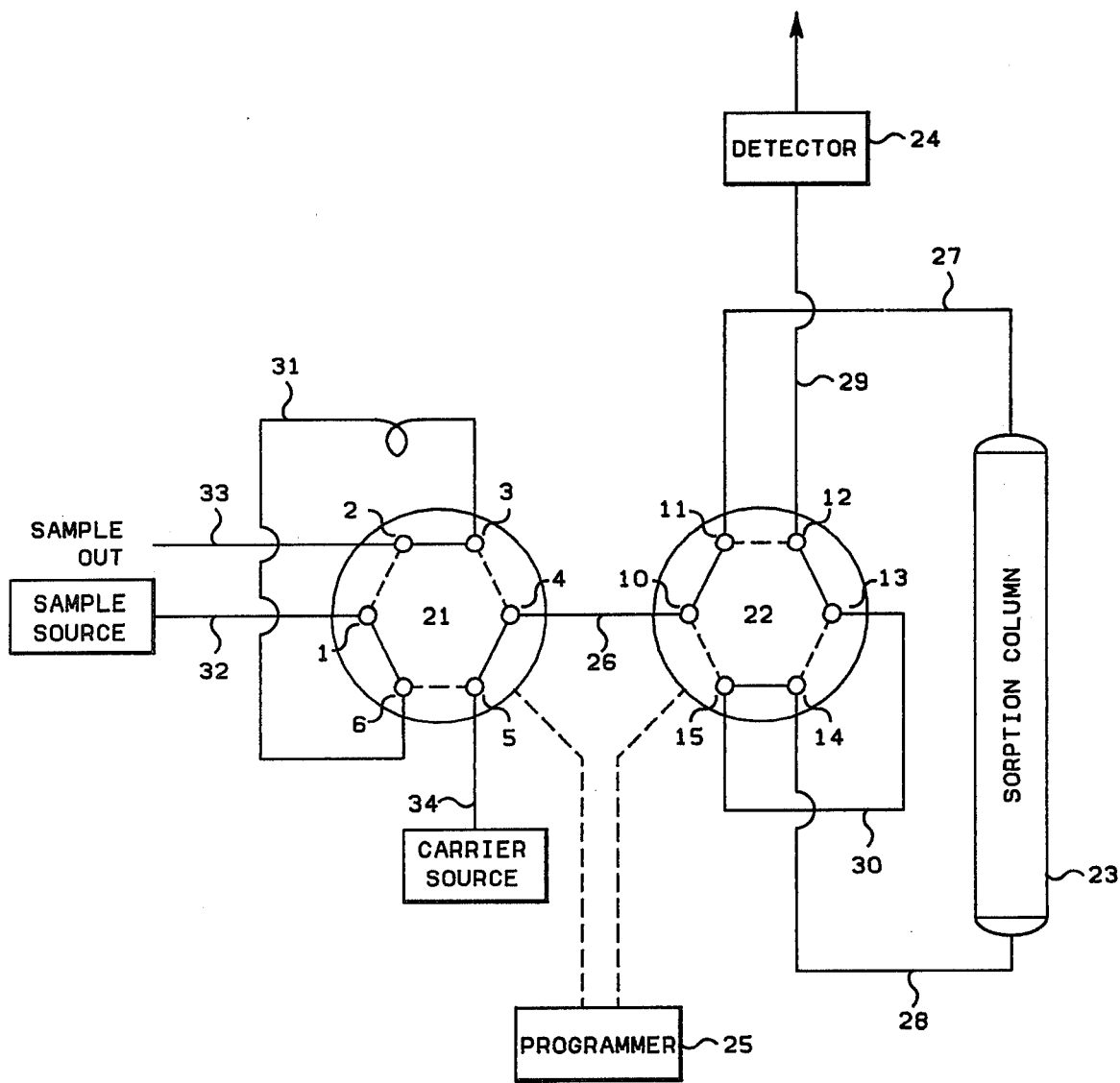

LIQUID COLUMN CHROMATOGRAPHIC SEPARATION

The present invention relates to liquid column chromatography. In one aspect this invention relates to liquid column chromatography as used in industrial process control.

In various industrial operations, there is a need for analytical procedures capable of continuously monitoring the concentration of certain constituents of process streams so that the industrial process can be controlled in response to the analysis. By means of liquid column chromatographic analysis, liquid samples continuously taken at chosen times from a process stream can be sequentially passed through a suitable chromatographic column for separation. The effluent from the column is then monitored by a suitable analyzer or detector. In order to assure that the materials separated are truly representative of the components of each sample, the chromatographic column can be flushed with a carrier liquid in such a fashion as to insure that no significant removable amounts of the preceding sample liquid components remain in the column.

It has been noted that in such continuous liquid column chromatography the passage of a plurality of samples through the column tends to compact the solid particulate sorbent in the column toward the outlet end of the column. Such compacting can alter the characteristics of the column so that one cannot be certain whether variations detected in the components of the various liquid samples are due the variations in the industrial process or to changes in the characteristics of the column. One technique which can be employed to minimize column compacting involves backflushing the column with carrier after each sample for about the same length of time as taken for the preceding sample separation. This backflushing operation, of course, renders the column unavailable for sample separation at least half the time.

An object of the present invention is to provide a method for countering the compacting of sorbent in a chromatographic column tht occurs during the sequential separation of a plurality of samples without rendering the column unavailable for sample separation for as long as is required when backflushing is used to counter compacting.

Another object is to provide a liquid column chromatographic separation system capable of countering compacting of sorbent in a chromatographic column that occurs during the sequential separation of a plurality of samples.

Other objects, aspects, and advantages of this invention will be apparent to one skilled in the art from a study of this disclosure and its accompanying drawing.

In accordance with the present invention, a plurality of liquid samples are subjected to chromatographic separation and analysis involving sequentially passing each liquid sample through at least a portion of a sorbent-containing column to effect for each such liquid sample elution of at least a portion of said sample components from the column in response to the relative affinity of those components for the sorbent in the column and analyzing at least a portion of the components of each liquid sample as the components are eluted from the column. In accordance with this invention, the direction of flow of the liquid samples through the column is periodically reversed in such a fashion that differences observed in the analysis of the various liquid samples can be attributed to differences in the composition of the liquid samples rather than differences in the compacting of the particulate sorbent in the column. The point in time at which reversal of flow for the samples in necessary can readily be determined by one skilled in the art by empirical study of the effect of the separation conditions on the particular sorbent using a liquid of known composition. In a preferred embodiment of the invention, the flow of liquid sample through the column is reversed with each liquid sample. It is also preferred that the time liquid flows through the column in one direction be equal to the time that liquid flows through the column in the opposite direction. The passage of each liquid sample, after the first, can be preceded by passing through the column a sufficient amount of a flushing liquid to insure that when the next liquid sample is passed through the column no removable amounts of the previous liquid sample components remain on the column which would result in the analysis reflecting something that was actually part of the previous liquid sample rather than the next liquid sample. To obtain maximum analysis in the least time the flow of flushing liquid between the respective liquid samples separations should, of course, be no longer in duration than is required to suitably clean the sorbent.

The liquid column chromatographic analysis system of the present invention involves:

(1) a first conduit means for connection to a source of sample liquid, (2) a second conduit means for connection to a source of carrier liquid, (3) a sample valve means having first and second exit ports, said sample valve means being so constructed and so connected to said first and second conduit means that when said sample valve means is in a first position sample liquid from said first conduit means can pass through a first passageway of said sample valve means to said first exit port of said sample valve and carrier liquid from said second conduit means can pass through a second passageway of said valve to said second exit port of said sample valve and when said sample valve means is in a second position said sample liquid from said first conduit can pass through a third passageway of said valve means to said first exit port and said carrier liquid from said second conduit can pass through said first passageway of said valve means to said second exit port so that when said sample valve is switched from said first position to said second position a predetermined amount of said liquid sample can pass through said first passageway to said second exit port along with said carrier liquid, (4) a third conduit means connected to the second exit port of said sample valve means, (5) a particulate sorbent-containing column having first and second ends, (6) a fourth conduit means connected to the first end of said column, (7) a fifth conduit means connected to the second end of said column, (8) a two-position column reversing valve means having six ports through which liquid can flow, said column reversing valve means having its first port connected to said third conduit means so that liquid can flow from said sample valve means into said column reversing valve, said second port being connected to said fourth conduit and the fifth port being connected to said fifth conduit so that in either position of said column reversing valve means liquid can flow in a cycle from said column reversing valve through said sorption column back into said column reversing valve, said column reversing valve means being such that in one position liquid entering said first port can flow to said second port, then through said fourth conduit means, then through said column, then through said fifth conduit means to said fifth port, then to the sixth port, then to the fourth port, and then to the third port and in the other position of said column reversing valve means liquid entering said first port can flow to said sixth port to said fourth port to said fifth port, then through said fifth conduit means, then through said column, then through said fourth conduit means, to said second port and then to said third port, (9) a detecting means for detecting a property of a liquid directed thereto;

(10) a sixth conduit means connecting said third port of said column reversing valve to said detecting means in such a fashion that liquid can flow from said third port to said means for detecting, and

(11) valve switching means for altering the position of said sample valve means and said column reversing means.

A further understanding of the present invention will follow from a discussion of the accompanying drawing. The drawing is a schematic representation of one embodiment of the present invention.

The system in the drawing comprises a sample valve 21, a column reversing valve 22, a sorption column 23, a detector means 24, and a programmer 25 for controlling the position of said sample valve 21 and said column reversing valve 22.

The sample valve 21 and the column reversing valve 22 are depicted schematically in the drawing as six-port, two-position valves. Detailed discussion of such valves can be found in U.S. Pats. Nos. 3,140,615 and 3,492,873, the disclosures of which are incorporated herein by reference. Air-actuated, six-port, two-position valves of this type can be obtained from Applied Automation, Inc. located in Bartlesville, Oklahoma.

It is to be noted that, instead of using a six-port, two-position valve as the sample valve 21, any suitable liquid sample valve could be employed. For example, one could employ a slide valve of the type described in U.S. Pat. No. 2,846,121, the disclosure of which is incorporated herein by reference.

The sorption column 23 can be any suitable chromatographic column containing a suitable solid particulate packing material capable of suitably selectively retarding the flow of the various components of the liquid samples that are to be tested.

The detector means 24 can be any suitable means which will detect a property which reflects the composition of a liquid that is directed thereto. The choice of the type of prior art detector is considered to be a matter of choice to be determined by the type of analysis that is desired. Typical detectors include refractometers and ultraviolet detectors.

The programmer 24 can be operated by a time cycle or by other means, for example, a signal from the detector 24 or from a flow meter monitoring the flow of liquid through the column could be used to initiate a suitable response by the programmer. Any number of conventional programmers generally used in chromatographic analysis would be suitable. A discussion of two such programmers can be found in U.S. Pat. No. 3,119,995 and 3,732,466, the disclosures of which are incorporated herein by reference. While it would not be particularly practical, the programmer could be replaced by a human being.

It will be understood that associated with the programmer there must be valve switching means which in response to the programmer will alter the position of the sample valve and the column valve. Although no valve switching means has been illustrated in the drawing, any suitable means can be employed. The solution of such means is well within the skill of those skilled in this area.

A port 4 of the sample valve 21 is connected to a port 10 of the column reversing valve 22 by a conduit means 26 in such a fashion that liquid can flow from said sample valve 21 into said column reversing valve 22. The sorption column 23 is connected to the column reversing valve 22 by conduit means 27 and 28 so that liquid from said column reversing valve 22 can flow through said column 23 and back into said column reversing valve 22. The detector 24 is in turn also connected to the column reversing valve 22 by means of a conduit means 29 which allows liquid from said column reversing valve 22 to flow to said detector 24.

The column reversing valve 22 includes a passageway 30 which allows communication between ports 13 and 15 of said column reversing valve 22.

The sample value 21 includes a sample loop passageway 31 which allows communication between ports 3 and 6 of said sample valve 21. Passageway 31 is of dimensions such that it has an internal volume equal to the volume of liquid sample to be subjected to separation and analysis.

Connected to port 1 of sample valve 21 is a conduit means 32 which is capable of introducing into the sample valve 21 a stream of the liquid that is to be tested from a source of that liquid, i.e., a process stream. Connected to port 2 of the sample valve 21 is a conduit means 33 which is capable of allowing the stream of the liquid to be tested to flow out of the sample valve for recycling to a process or for suitable discarding.

Connected to port 5 of the sample valve 21 is a conduit means 34 which allows carrier liquid from a source to flow into said sample valve 21.

A preferred method of operation of the illustrated system will now be explained by referring to the changes in liquid flow path that can be provided by such a system. In order to obtain a suitable amount of sample liquid for chromatographic separation, the sample valve means 21 in response to the previously programmed programmer 25 is positioned such that the sample liquid supplied via conduit 32 enters the sample valve 21 at port 1 and travels from there to port 6 and on through sample loop passageway 31, port 3, and port 2 in sequence to exit the sample valve 21 into conduit means 33. With the sample valve 21 in that portion the carrier liquid provided by conduit means 34 is passed from port 5 to port 4 from where the carrier liquid travels in sequence through conduit 26, the column reversing valve 22, the column 23, the column reversing valve 22, and the detector 24. A programmer 25, programmed so that after passageway 31 of the sample valve means 21 has been filled with liquid from the sample source, the sample valve means 21 is switched to its other, or second, position. In the switching of the sample valve 21 from its first position to its second position, a specific volume of the liquid to be sampled is trapped in passageway 31.

When the sample valve means is in this second position, liquid from the sample source flowing into the sample valve 21 flows directly from port 1 to port 2 and then into conduit 33. Simultaneously in this second position the carrier liquid flows from port 5 in sequence through port 6, passageway 31, port 3, and port 4. By so redirecting the flow of carrier liquid the trapped volume of liquid sample is carried out of the sample valve 21 by the carrier liquid. Although other timing arrangements can be used, preferably the sample valve 21 is left in this second position only until said carrier liquid forces the liquid sample out of the sampling valve 26 and into the column 23. The sampling valve is then switched to its first position in which the carrier liquid flows from port 5 to port 4 to conduit 26. The carrier flow is maintained so that the components of the liquid sample will be separated on the column and pass through the column reversing valve 22 to the detector 24. For example, in one position the column reversing valve receives liquid from the sample valve 21 and passes that liquid through conduit means 27, then through the column 23, then through conduit means 28, then back through the column reversing valve 22, then through conduit valve 29 to the detector means 24.

After the separation and analysis of the liquid components is suitably complete, the programmer 25 causes the column reversing valve to switch to its other position, whereupon carrier liquid will flow through the column reversing valve means and into the column 23 via conduit 28 so that a reversal of flow in the column 23 is achieved. At a preselected time interval, for example, that deemed sufficient to insure that when a new liquid sample is passed through the column 23 no significant removable amounts of the previous liquid sample components remain on the column, the programmer 25 again switches the sample valve 21 from its first to its second position and back to its first in such a fashion that again a specific volume of liquid sample is carried from said sample valve 21 to said column reversing valve 22. The switching of the sample valve 21 and the column reversing valve 22 is then continued as above described in such a fashion that the liquid flow through the column in one direction is substantially equal to the liquid flow through the column in the other direction so that the tendency of the particulate sorbent to compact toward one end is minimized.

It is to be understood that the attached drawing and the foregoing description thereof have been provided solely for illustrating one embodiment of the present invention and are not intended to unduly limit the present invention. Various modifications within the scope of the present invention will be obvious to those skilled in the art after reading this disclosure. For example, while in the above discussion in reference to the drawing the direction of liquid flow as changed after each sample, the changes in the liquid flow direction in the column could be limited to any periods found to be necessary to keep the particulate sorbent from being exposed to an undesirable amount of compacting.

What is claimed is:

1. A process for sequentially subjecting a plurality of liquid samples to chromatographic separation and analysis comprising sequentially passing each liquid sample through at least a portion of a column packed with particulate sorbent to effect for each said liquid sample elution of at least a portion of the components of each said liquid sample from the column in response to the relative affinity of said components for the sorbent, and analyzing at least a portion of the components of each said liquid sample as said portion of the components is eluted from said column, wherein periodically the point of introduction of liquid sample into the column is reversed in such a fashion that differences observed in the analysis of the various liquid samples can be attributed to differences in the liquid samples rather than differences due to compacting of the particulate sorbent in the column.

2. A process according to claim 1 wherein a flushing liquid is passed at least partially through the column after each sample in an amount sufficient to insure that when the next liquid sample is passed through said column no removable amounts of the previous liquid sample components remain in the column which would result in the analysis reflecting something that was part of the previous liquid sample.

3. A process according to claim 2 wherein the flushing liquid is flowed through the column in the same direction as the flow of the preceding liquid sample.

4. A process according to claim 2 wherein the flushing liquid is flowed through the column in a direction opposite to the flow of the preceding liquid sample.

5. A process according to claim 4 wherein the flow of said flushing liquid through the column is initiated in response to the analysis of the preceding liquid sample components.

6. A process according to claim 4 wherein the flow of flushing liquid through the column is initiated at preselected suitable time intervals.

7. A process according to claim 4 wherein the flow of liquid sample through the column is reversed for each liquid sample.

8. A process according to claim 7 wherein the liquid sample is passed through the sorbent-containing column with a carrier liquid.

9. A process according to claim 8 wherein the carrier liquid is employed as the flushing liquid.

10. A process according to claim 9 wherein the time of liquid flows through said column in one direction is equal to the time of liquid flows through the column in the opposite direction.

11. A process according to claim 10 wherein the flow of flushing liquid through the column is initiated at preselected time intervals.

12. A process according to claim 11 comprising (1) positioning a sample valve containing a trapped amount of a liquid sample so that a carrier liquid can flow through said sample valve in such a fashion as to force said liquid sample out of said sample valve, (2) passing said carrier liquid through the thus-positioned sample valve, through a column reversing valve, then through said column, then back through said column reversing valve; and finally through an analyzing zone, until the desired amount of liquid components is forced by said carrier liquid through the column to the analysis zone, (3) then switching the column reversing valve to another position which will allow carrier liquid to flow through said column reversing valve, then through said column in a direction opposite its previous flow through said column, then back through said column reversing valve, and finally to said analyzing zone, (4) passing said carrier liquid through the flow path provided by the thus-positioned column reversing valve until a sufficient amount of carrier liquid has flowed through the column to insure that any significant removable components will be removed from the column before another liquid sample is supplied to the column, (5) positioning said sample valve so that it will trap a specific amount of a liquid sample from a liquid sample source while at the same time allowing said carrier liquid to flow through said sample valve to said column reversing valve, (6) supplying a liquid sample to said sample valve and trapping said specific amount of said liquid sample while also passing said carrier liquid through said sample valve to said column reversing valve, and (7) repeating at least once steps (1) through (6).

13. A liquid column chromatographic analysis system comprising:
(1) a first conduit means for connection to a source of sample liquid,
(2) a second conduit means for connection to a source of carrier liquid,
(3) a sample valve means having first and second exit ports, said sample valve means being so constructed and so connected to said first and second conduit means that when said sample valve means is in a first position sample liquid from said first conduit means can pass through a first passageway of said sample valve means to said first exit port of said sample valve means and carrier liquid from said second conduit means can pass through a second passageway of said sample valve means to said second exit port of said sample valve means and when said sample valve means is in a second position said sample liquid from said first conduit means can pass through a third passageway of said sample valve means to said first exit port and said carrier liquid from said second conduit means can pass through said first passageway of said sample valve means to said second exit port so that when said sample valve means is switched from said first position to said second position a predetermined amount of said liquid sample can pass through said first passageway to said second exit port along with said carrier liquid,
(4) a third conduit means connected to the second exit port of said sample valve means,
(5) a particulate sorbent-containing column having first and second ends,
(6) a fourth conduit means connected to the first end of said column,
(7) a fifth conduit means connected to the second end of said column,
(8) a two-position column reversing valve means having six ports through which liquid can flow, said column reversing valve means having its first port connected to said third conduit means so that liquid can flow from said sample valve means into said column reversing valve, said second port being connected to said fourth conduit means and said fifth port being connected to said fifth conduit means so that in either position said column reversing valve means liquid can flow in a cycle from said column reversing valve means through said sorption column back into said column reversing valve means, said column reversing valve means being such that in one position liquid entering said first port can flow to said second port, then through said fourth conduit means, then through said column, then through said fifth conduit means to said fifth port, then to said sixth port, then to said fourth port, and then to said third port and in the other position of said column reversing valve means liquid entering said first port can flow to said sixth port to said fourth port to said fifth port, then through said fifth conduit means, then through said column, then through said fourth conduit means, to said second port, and then to said third port,
(9) a detecting means for detecting a property of a liquid directed thereto.
(10) a sixth conduit means connecting said third port of said column reversing valve to said detecting means in such a fashion that liquid can flow from said third port to said means for detecting, and
(11) valve switching means for altering the position of said sample valve means and said column reversing valve means.

14. A system according to claim 13 having a programming means for activating said valve switching means.

15. A system according to claim 14 wherein said programming means operates at least in part in response to a signal from said detecting means.

16. A system according to claim 13 wherein said sample valve means comprises a six-port two-position valve.

17. A process for sequentially subjecting a plurality of liquid samples to chromatographic separation and analysis comprising (1) positioning a sample valve containing a trapped amount of a liquid sample so that a carrier liquid can flow through said sample valve in such a fashion as to force said liquid sample out of said sample valve, (2) passing said carrier liquid through the thus-positioned sample valve, through a column reversing valve, then through said column, then back through said column reversing valve, and finally through an analyzing zone, until the desired amount of liquid components is forced by said carrier liquid through the column to the analysis zone, (3) then switching the column reversing valve to another position which will allow carrier liquid to flow through said column reversing valve, then through said column in a direction opposite its previous flow through said column, then back through said column reversing valve, and finally to said analyzing zone, (4) passing said carrier liquid through the flow path provided by the thus-positioned column reversing valve until a sufficient amount of carrier liquid has flowed through the column to insure that any significant removable components will be removed from the column before another liquid sample is supplied to the column, (5) positioning said sample valve so that it will trap a specific amount of a liquid sample from a liquid sample source while at the same time allowing said carrier liquid to flow through said sample valve to said column reversing valve, (6) supplying a liquid sample to said sample valve and trapping said specific amount of said liquid sample while also passing said carrier liquid through said sample valve to said column reversing valve, and (7) repeating at least once steps (1) through (6) in such a fashion that the differences observed in the analysis of the various liquid samples can be attributed to differences in the liquid samples rather than differences due to compacting of the particulate sorbent in the column.

* * * * *